United States Patent [19]

Dassler et al.

[11] Patent Number: 4,807,995
[45] Date of Patent: Feb. 28, 1989

[54] PROCESS FOR ELECTRO OPTICAL INSPECTION OF THE MOUTH AREA OF GLASS BOTTLES

[75] Inventors: Hans-Ulrich Dassler, Oberschleissheim; Ruediger Haas, Faistenhaar; Gerhard Loeffler, Munich; Lutz Liebers, Bergneustadt, all of Fed. Rep. of Germany

[73] Assignee: OEM Messtechnik GmbH, Fed. Rep. of Germany

[21] Appl. No.: 882,229

[22] Filed: Jul. 7, 1986

[30] Foreign Application Priority Data

Jul. 4, 1985 [DE] Fed. Rep. of Germany ....... 3523975

[51] Int. Cl.[4] ............................................ G01N 21/90
[52] U.S. Cl. ............................... 356/240; 250/223 B; 209/526
[58] Field of Search ............................. 356/428, 240; 250/223 B; 209/526

[56] References Cited

U.S. PATENT DOCUMENTS

| | | |
|---|---|---|
| 3,069,553 | 2/1962 | Zoltanski . |
| 3,255,740 | 2/1966 | Rottmann ........................ 250/223 B |
| 3,479,514 | 11/1969 | Kidwell ........................... 250/223 B |
| 4,208,130 | 6/1980 | Saconney et al. ................... 356/428 |
| 4,213,702 | 7/1980 | Bryant et al. .................... 250/223 B |
| 4,391,373 | 7/1983 | Wiggins .......................... 250/223 B |
| 4,492,476 | 1/1985 | Miyazawa . |
| 4,650,326 | 3/1987 | Nagamine et al. . |
| 4,701,612 | 10/1987 | Sturgill ........................... 250/223 B |

FOREIGN PATENT DOCUMENTS

| | | | |
|---|---|---|---|
| 0047936 | 3/1982 | European Pat. Off. ........... 356/428 |
| 2516138 | 10/1976 | Fed. Rep. of Germany . |
| 3228464 | 7/1982 | Fed. Rep. of Germany . |
| 3422870 | 1/1985 | Fed. Rep. of Germany . |
| 0063438 | 4/1982 | Japan ................................. 356/428 |
| 217141 | 7/1984 | Japan . |

Primary Examiner—Vincent P. McGraw
Assistant Examiner—S. A. Turner
Attorney, Agent, or Firm—Robert J. Koch

[57] ABSTRACT

A bottle is moved over a sector of a circular path and simultaneously rotated around its longitudinal axis for the opto-electronic inspection of the mouth area for chipping of the glass. The bottle is guided through the beam path of a measuring apparatus on its way over the circular path. A measuring beam passes at an oblique angle to the longitudinal axis of the bottle in the area of the mouth opening. The location dependent scanning signal generated by the measuring apparatus during each scan corresponding to every discrete angular position of the bottle displays a characteristic intensity modulation. The presence of a chip in the glass may be recognized in the scanning signal by the absence of the intensity maximum present at the location of a chip. The absence of the intensity maximum may be ascertained by measuring the distance between two adjacent intensity maxima and comparing the measured distance with a reference value.

4 Claims, 1 Drawing Sheet

PROCESS FOR ELECTRO OPTICAL INSPECTION OF THE MOUTH AREA OF GLASS BOTTLES

BACKGROUND OF THE INVENTION

1. Field of the Invention

The invention relates to a process for opto-electronic inspection of bottles, and more particularly to a process for inspection of portions of bottles such as sealing rims and/or threads.

2. Description of the Related Art

In a known opto-electronic inspection system according to DE- No. 3,228,464, the disclosure of which is incorporated herein, the side walls of cleaned glass bottles are inspected for residual impurities by moving each bottle on a circular path through a beam between a diffuse source of light and an electronic image converter and simultaneously rotating said bottle 360° with respect to its longitudinal axis for development of its entire side wall. The image converter, which consists of a photodiode camera and a scanner (rotating mirror), follows the advance motion of the bottle synchronously and is continuously aligned with the longitudinal axis of the bottle tested. Each scanning signal of the image converter generated in a defined angular rotating position of the bottle represents a sequence of image points located above each other (line of light) and constitutes an image of two radially opposing partial surfaces of the side wall of the bottle. Any contamination of the side wall causes a break in the intensity of the scanning signal at the point in the signal generated by the photodiodes in the row located in the beam path through the impurity which otherwise is practically constant. To determine the presence of an impurity, it is merely necessary to compare the intensity level of every scanning signal with a minimum level, wherein any signal below the minimum level identifies a break in the intensity and thus an impurity. In place of a row of diodes and a scanner following the bottle moving on a circular path, more recently an array of diodes has been used. The array consists of a plurality of adjacent rows of photodiodes, the width whereof covers the entire range of observation.

The known side wall inspector is not capable of observing or inspecting the mouth area of a glass bottle. This mouth area includes the annular surface around the mouth of the bottle serving as the tightening surface for both crown cork and screw cap closures. In bottles exhibiting thread closures, for example mineral water bottles, the mouth area also includes the bottle thread. Large chips of the glass in the annular sealing surface or the bottle thread interferes with the normal closing of the bottle, therefore it is important to separate bottles with such chips prior to the filling process. Known mouth inspection devices which produce a television image of a view of the mouth are only able to inspect the sealing surface, not the bottle thread. However, even the inspection of the sealing surface is inaccurate due to inadequate defect resolution because only the light reflected by the bottle mouth resulting from the necessary illumination from above impacts the optics of the television camera. This light is of insufficient intensity to enable measuring detection of intensity differences produced by chipped glass.

SUMMARY OF THE INVENTION

It is an object of the invention to provide a process for inspection of the mouth area of glass bottles for chipping in a manner such that the detection of defects is significantly improved in relation to the known bottle/mouth inspection means. According to the invention, conventional inspection systems such as shown in DE- No. 3,228,464 may be modified in a novel fashion to achieve this result.

This object may be attained according to the invention by a process where a bottle is moved over a sector of a circular path and simultaneously rotated around its longitudinal axis. The bottle is illuminated during its rotation around its longitudinal axis by a source of light emitting a diffuse beam. The light passing through the longitudinal axis of the bottle is sequentially scanned by a row of photodiodes or an array of photodiodes and each scanning signal which represents a sequence of image point located above each other or lines of light, respectively, is evaluated to detect an error or chip.

The mouth area of the bottle may optionally include a screw thread and is illuminated and optically scanned to detect chipping. The illumination is directed at an oblique angle in a highly diffuse manner. The illumination's intensity is modulated by the characteristics of the bottle and scanned by the diodes. The diodes generate a scanning signal which is evaluated to determine whether the distance between two adjacent intensity maxima is larger or smaller than a reference value. A chip in the glass is identified when a distance value exceeding said reference value is detected.

The invention will become more apparent from the disclosed embodiment with reference to the drawings.

DETAILED DESCRIPTION OF THE PREFERRED EMBODIMENT

Figure 1:
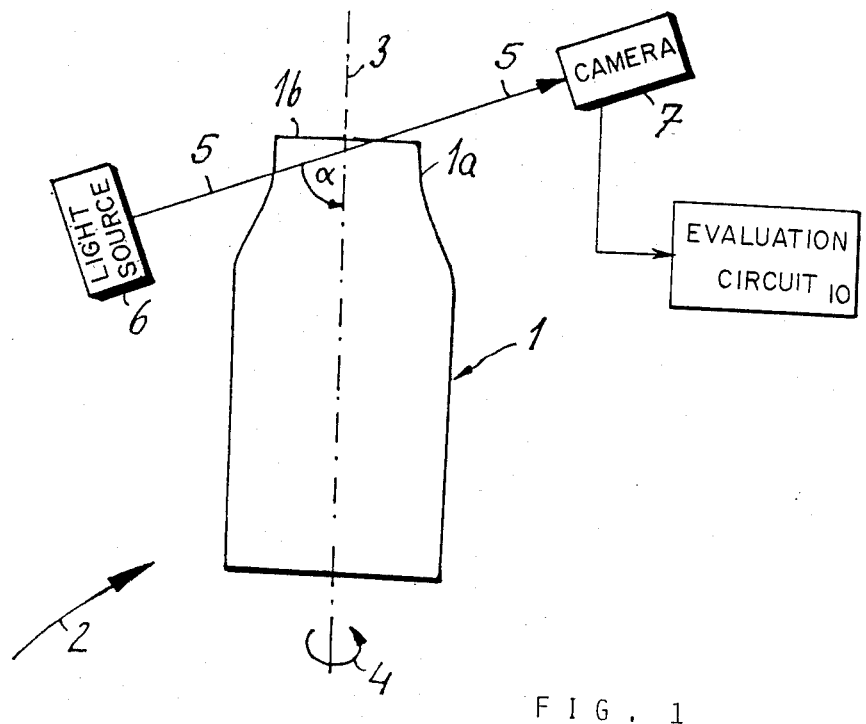
FIG. 1 shows a schematic view of the measuring beam path through a glass bottle in the process according to the invention.

FIG. 1 shows a schematic view of a glass bottle 1, exhibiting a bottle thread 1a and an annular sealing surface 1b in the mouth area. The bottle 1 is moved along a circular path indicated by the arrow 2 and simultaneously rotated around its longitudinal axis 3, which is indicated by the arrow 4. The bottle 1 passes with its mouth area 1a/1b through the measuring beam 5 between a highly diffuse source of light 6 and a photodiode camera 7 on its way along the circular path 2. The camera 7 may contain either a row of photodiodes and a scanner synchronously following the motion of the bottle, or an array of photodiodes covering the entire range of bottle movement.

It is essential that the beam 5, scanned by the camera 7, extend through or intersect the longitudinal axis 3 and be oriented at an oblique angle to the longitudinal axis 3 of the bottle. The beam 5 passes through both the bottle thread 1a and the annular sealing surface 1b as a result of this oblique angle illumination of the bottle 1. The light source 6 is located as close as possible to the bottle 1, in order to obtain a high diffusor effect.

Figure 2:
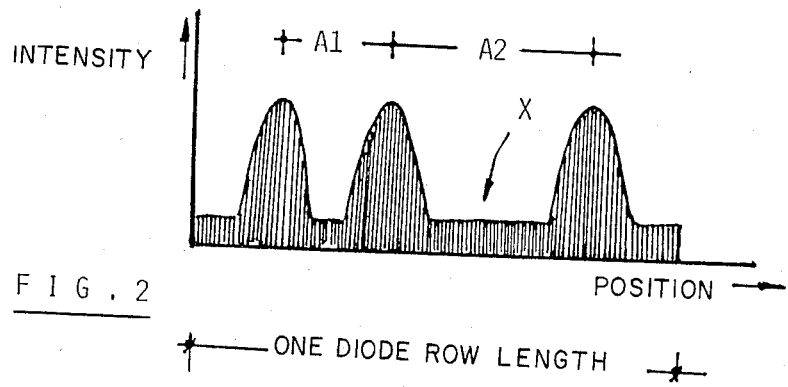
FIG. 2 shows the location dependent progress of a scanning signal generated and evaluated according to the invention.

The electric signal generated by the camera 7 during each scanning, i.e., in every defined rotation angle position of the bottle 1, is evaluated by an evaluation circuit 10 and shown schematically in FIG. 2. It includes a number of light intensity values corresponding to the number of photodiodes per row, with the form of the signal produced by the sequential reading out of the photodiodes. The signal displayed is thus location dependent, provided that the row of diodes is oriented parallel to the longitudinal axis 3 of the bottle.

It is essential that the envelope generating curve of the signal shown in FIG. 2 exhibit an explicit intensity modulation. The characteristic feature is that there is no intensity maximum at the location of a chip in the area of the thread 1a of the bottle 1. Such a defect location is indicated in the signal illustrated in FIG. 2 by "X". The distance "A" between two adjacent intensity maxima is detected and compared with a reference value in order to determine the characteristic absence of a maximum in the signal according to FIG. 2 and thus the existence of a chip in the glass. In the case of FIG. 2, the distance A1 is below this reference value and the distance A2 above it. The excess of A2 over the reference value identifies the chip in the glass at location "X".

It has been found that the determination of glass chips in the mouth area 1a/1b according to the above-described process of the invention makes extremely accurate detection of glass chips possible, in particular relatively small chips in the bottle thread 1a and the sealing surface 1b. The process is far superior to known bottle mouth inspecting devices, which are capable of inspecting only the sealing surface.

Although the signal display in FIG. 2 is valid for the conditions prevailing in the case of a bottle with thread closure, the process is also applicable to bottles with crown cork closures, as local intensity modulations similar to those of FIG. 2 also result in such bottles.

We claim:

1. A process for opto-electronic inspection of bottles comprising the steps of:
   moving a bottle over a sector of a circular path and simultaneously rotating the bottle around a longitudinal axis thereof;
   illuminating said bottle during the rotation around said longitudinal axis by a source of light emitting a diffuse beam at an oblique angle to said longitudinal axis in a mouth area of said bottle;
   sequentially scanning light passing through the longitudinal axis of the bottle by an arrangement of photodiodes generating a scanning signal; and
   evaluating intensity modulation of said scanning signal by comparing distance between intensity maxima with a reference value and identifying a chip in said bottle upon said distance exceeding said reference value.

2. A process as in claim 1 wherein said mouth area exhibits screw threading and said step of illuminating includes illumination of said screw threading.

3. A process as in claim 1 wherein said arrangement of photodiodes is a row of photodiodes.

4. A process as in claim 1 wherein said arrangement of photodiodes is a photodiode array.

* * * * *